United States Patent [19]

Cohen

[11] 3,954,834

[45] May 4, 1976

[54] ALICYCLIC KETOESTERS AND PROCESS FOR THEIR MANUFACTURE

[75] Inventor: Amnon Mordechai Cohen, Amersfoort, Netherlands

[73] Assignee: Polak's Frutal Works N.V., Amersfoort, Netherlands

[22] Filed: Nov. 26, 1973

[21] Appl. No.: 418,868

Related U.S. Application Data

[63] Continuation of Ser. No. 195,476, Nov. 3, 1971, abandoned.

[30] Foreign Application Priority Data

Nov. 4, 1970 United Kingdom............... 52388/70

[52] U.S. Cl............................. 260/468 K; 260/464; 260/514 K; 260/586 R; 252/522

[51] Int. Cl.².......................................... C07C 69/74

[58] Field of Search ................................ 260/468 K

[56] References Cited

UNITED STATES PATENTS 3,158,644 11/1964 Demele et al....................... 260/468

*Primary Examiner*—Robert Gerstl

*Attorney, Agent, or Firm*—William S. Alexander; Clinton F. Miller

[57] ABSTRACT

New alicyclic ketoesters having the generic formula

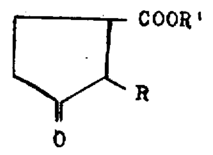

wherein R represents a hydrocarbon radical containing from 4 to 8 carbon atoms, and R′ represents an alkyl radical containing from 1 to 2 carbon atoms, are prepared, in one embodiment, by condensing the methyl or ethyl ester of propane-1,2,3-tricarboxylic acid with methyl or ethyl esters of 2-bromo acids containing from 6 to 10 carbon atoms, and hydrolyzing, decarboxylating and re-esterifying the resulting cyclic keto-triesters.

The new compounds have olfactory properties and are useful in the production of a great variety of perfumes.

11 Claims, No Drawings

ALICYCLIC KETOESTERS AND PROCESS FOR THEIR MANUFACTURE

This is a continuation of application Ser. No. 195,476, filed Nov. 3, 1971, now abandoned.

This invention relates to new cyclic ketoesters, more particularly to methyl and ethyl esters of 2-alkyl-3-oxo-cyclopentanecarboxylic acids, which possess interesting olfactive properties and which therefore are useful in the preparation of a great variety of perfume compositions.

The compounds of this invention can be represented by the following general formula:

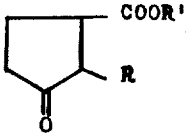

I wherein R represents a hydrocarbon radical having from 4 to 8 carbon atoms and R′ represents methyl or ethyl. The substituent represented by R in the above formula I can be a straight-chain radical such as an n-butyl, n-pentyl, n-hexyl, n-heptyl, n-octyl or a branched alkyl radical i.e. a secondary or a tertiary alkyl radical; or a cycloaliphatic radical.

The ketoesters represented by formula I can be prepared by condensing methyl or ethyl ester of propane-1,1,3-tricarboxylic acid with methyl or ethyl esters of 2-bromoacids having from 6 to 10 carbon atoms. The resulting cyclic keto-triesters on hydrolysis, decarboxylation and re-esterification yield the corresponding ketoesters I. This synthesis can be illustrated by the following reaction scheme:

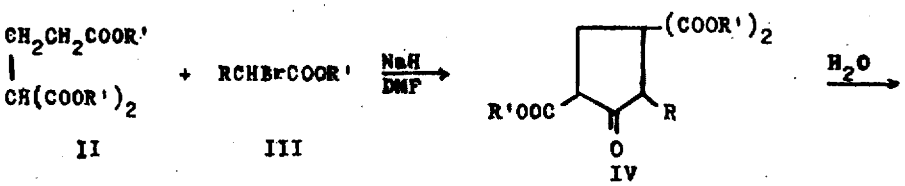

II III IV

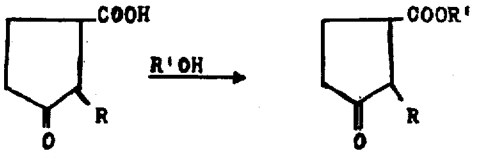

V I

The condensation of triesters II with α-bromoesters III can be conducted in the presence of any basic agent which promotes the "malonic ester synthesis" type reaction in both polar and apolar solvents. However, of a great variety of basic reagents in different solvents, sodium hydride in dimethylformamide was found to be the most effective. The starting triesters II and the bromoesters III used for carrying out this process are known compounds. The triesters II are made by Michael addition of malonic esters to the corresponding esters of acrylic acid (I. N. Nazarov and S. I. Zav'yalov, Izvest.Akad.Nauk.S.S.S.R., Otdel.Chim.Nauk, 300 (1952); G. A. Swan, J.Chem.Soc., 1039 (1955); F. L. M. Pattison, R. L. Buchanan and F. H. Dean, Can.J.-Chem. 43(6), 1700 (1965)). The bromoesters III are made by bromination of the corresponding fatty acids or halides and esterification of the resulting bromoacids or bromoacyl halides (Houben-Weyl), "Methoden der organischen Chemie", Vol. V/4, p. 197, Thieme, Stuttgart 1960).

Part of the intermediate ketoacids represented by formula V are also known compounds although prepared via a different and more laborious method (R. Giuliano, M. Artico, and A. Ermilli, Ann.Chim. (Rome), 50, 1453 (1960).

The ketoesters represented by formula I can also be prepared by reacting 2-alkyl-2-cyclopentanones with hydrogen cyanide or a hydrogen cyanide generating compound to yield the corresponding cyclic ketonitriles, which are further converted by corresponding ketoesters. This synthesis can be represented by the following reaction scheme:

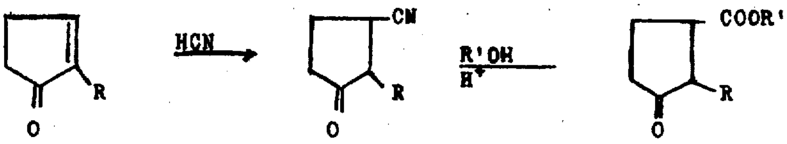

VI VII I

The addition of hydrocyanic acid to the unsaturated ketones VI can be effected by means of liquid hydrocyanic acid or of cyanide of potassium and sodium in the presence of an acid.

An alternative way is reacting VI with acetone cyanohydrin in the presence of an aqueous solution of sodium carbonate.

The ketonitriles described in this invention are new compounds.

The ketoesters I can be obtained from the corresponding nitriles by employing any of the various methods known for the alcoholysis of nitriles.

Most of the starting 2-alkyl-2-cyclopenanones used for carrying out this process are known compounds. As far as they are new, known methods can be employed for their preparation.

The ketoesters represented by formula I can further be prepared by reacting 2-alkyl-2-cyclopentanones with nitromethane to yield the corresponding nitroketones, which are further converted, in a modified Victor Meyer type reaction, into the corresponding keto-esters. This synthesis can be represented by the following reaction scheme:

propane-1,1,3-tricarboxylate (G. A. Swan, J.Chem.-Soc., 1039 (1955)) is added dropwise with vigorous stirring. The rate of addition is adjusted to maintain an internal temperature of about 25°C. The reaction mixture is stirred at room temperature until all the sodium hydride has reacted. 60 g of ethyl α-bromocaprylate (K. Bernhard, Helv.Chim.Acta, 29, 1462 (1946)) are added over a period of 1 hour. After the addition has been completed, the reaction mixture is stirred at 100°C for 5 hours. The reaction mixture is cooled to 10°C and added dropwise to a well stirred suspension of

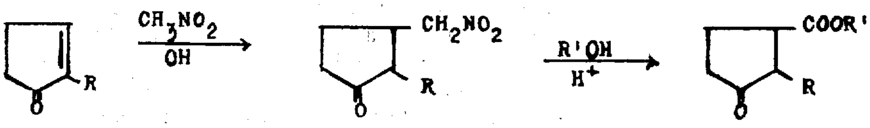

VI VIII I

The addition of nitromethane to the 2-alkyl-2-cyclopentanones VI can be conducted in the presence of a great variety of basic catalysts in different solvents, of which benzyltrimethylammonium hydroxide was found to be the most effective. The nitroketones represented by formula VIII are new compounds.

The alcoholysis of the nitroketones to the ketoesters I can be carried out by heating the nitroketones with the corresponding alcohols in the presence of an equivalent amount of a great variety of either mineral or organic acids.

The keto-esters of this invention are new fragrant substances possessing very characteristic olfactive properties. They develop a distinct floral odour which grows unexpectedly to a very exalting fragrance on standing on evaporation blotter-strips etc.; the new compounds demonstrate their fragrance-modifying power by developing interesting new notes when mixed with numerous other odoriferous materials and compositions of the floral, woody and/or fancy types. Owing to their fixative properties they are capable of developing longlasting and tenacious elegant notes to many perfumes. Owing to these properties the new compounds, when used in compositions, have the particular advantage that they permit a reduction in the proportions of natural flower concretes and absolutes. Depending on the odour type of the composition the new esters produce their desired effects within the very wide range of 0.1 to 10%.

In floral bases used as additives for other compositions, the new compounds can be used in proportions of 30% or more by weight.

EXAMPLE 1

Preparation of methyl 2-n-hexyl-3-oxo-cyclopentanecarboxylate a. Preparation of 2-n-hexyl-3-oxo-cyclopentanecarboxylic acid In a 1 L three necked flask fitted with a mechanical stirrer, a thermometer, a nitrogen inlet tube and a calcium chloride drying tube, is placed a suspension of 5.75 g of sodium hydride in 250 ml of dry dimethylformamide. Dry nitrogen is let in and 69 g of ethyl 5.75 g of sodium hydride in 50 ml of pentane under nitrogen atmosphere over a period of 2 hours. When the addition is completed, the mixture is stirred at room temperature for an additional 12 hours. The solvent is removed at a reduced pressure and the residue is poured into 1500 ml of cold 5% hydrochloric acid. The organic layer is separated and the water phase is extracted with ether. The combined organic layer and the ether extract are washed with water and sodium carbonate solution and dried over anhydrous sodium sulphate. After removal of the solvent, the unreacted ethyl propane-1,1,3-tricarboxylate is distilled off at 100°–105°C/0,15 mm (16 g) and the residue is boiled for 20 hours with a mixture of 750 ml of acetic acid and 750 ml of concentrated hydrochloric acid. The volatile acids are distilled off at a reduced pressure and the residue is poured onto a large excess of crushed ice. The solid product is collected on a Büchner funnel, washed repeatedly with cold water and dried. The product is recrystallized from cyclohexane-pentane to yield 21,5 g (78%) of 2n-hexyl-3-oxo-cyclopentanecarboxylic acid melting at 73°–74°C.

b. Preparation of methyl 2-n-hexyl-3-oxo-cyclopentanecarboxylate

A solution of 17 g of 2-n-hexyl-3-oxo-cyclopentanecarboxylic acid, 10 ml of methanol and 1 g of concentrated sulphuric acid in 50 ml of ethylene chloride, is refluxed for 8 hours. The reaction mixture is then washed with water and sodium carbonate solution and dried over anhydrous sodium sulphate. The solvent is distilled off at a reduced pressure and the residue is distilled through a short Vigreux column. The product, methyl 2-n-hexyl-3-oxo-cyclopentanecarboxylate is collected at 85°C/0,06 mm, yield 17 g (93%), $n_D^{20}$ 1.4562.

EXAMPLE 2

Preparation of ethyl 2-n-hexyl-3-oxo-cyclopentanecarboxylate

In a 1 L flask, to which is attached a water separator under a reflux condenser, is placed a solution of 20 g of 2-n-hexyl-3-oxo-cyclopentanecarboxylic acid, 9,5 g of absolute ethanol and 1 g of p-toluenesulphonic acid in 500 ml of benzene. The reaction mixture is refluxed until no more water separates. The reaction mixture is then cooled and washed successively with water and sodium carbonate solution and dried over anhydrous sodium sulphate. The solvent is removed by distillation at atmospheric pressure and the residue is distilled through a short Vigreux column. Ethyl 2-n-hexyl-3-oxo-cyclopentanecarboxylate is collected at 102°C/0.25 mm, yield 19,5 g (86%), $n_D^{20}$ 1.4535.

EXAMPLE 3

Preparation of methyl 2-n-pentyl-3-oxo-cyclopentanecarboxylate a. Preparation of 2-n-pentyl-3-oxo-cyclopentanecarboxylic acid By repeating the procedure described in Example 1(a) but starting from 195 g of methyl propane-1,1,3-tricarboxylate (F. L. M. Pattison, R. L. Buchanan and F. H. Dean, Can. J. Chem. 43(6), 1700 (1965)) and 176 g of methyl α-bromoheptanoate (H. Reinheckel, Ber. 93, 2222 (1960)), there is obtained 60 g (41%) of 2-n-pentyl-3-oxo-cyclopentanecarboxylic acid, melting at 52°C.

b. Preparation of methyl 2-n-pentyl-3-oxo-cyclopentanecarboxylate

By repeating the procedure described in Example 1 (b) but starting from 25 g of 2-n-pentyl-3-oxo-cyclopentanecarboxylic acid, there is obtained 23 g (86%) of methyl 2-n-pentyl-3-oxo-cyclopentanecarboxylate, boiling at 75°C/0,15 mm, $n_D^{20}$ 1.4557.

EXAMPLE 4

Preparation of ethyl 2-n-pentyl-3-oxo-cyclopentanecarboxylate

By repeating the procedure described in Example 2 but starting from 25 g of 2-n-pentyl-3-oxo-cyclopentanecarboxylic acid, there is obtained 24 g (89%) of ethyl 2-n-pentyl-3-oxo-cyclopentanecarboxylate, boiling at 79°C/0,1 mm, $n_D^{20}$ 1.4527.

The homologous alicyclic keto-esters and the corresponding intermediate alicyclic keto-acids listed in Table I, were prepared following the general methods described above.

EXAMPLE 9

Preparation of 2-n-hexyl-3-cyanocyclopentanone (Method A)

A mixture of 16,6 g of 2-n-hexyl-2-cyclopentenone (see foot note (1) under Table II) 12 g of acetone cyanhydrine (Org.Synth.Coll. Vol. 2, p. 7), 32 ml of methanol and 0,8 g of sodium carbonate in 12 ml of water, is heated at reflux temperature for 3½ hours.

The reaction mixture is then cooled to room temperature and poured into ice-cold water. The organic layer is separated and the water layer is extracted with ether. The combined organic layer and other extract are washed with water and dried over anhydrous sodium sulphate. The solvent is removed at atmospheric pressure and the residue is distilled through a short Vigreux column. The product is collected at 106°C/0,1 mm, yield 16 g (82%), $n_D^{20}$ 1.4658.

EXAMPLE 10

Preparation of 2-n-hexyl-3-cyanocyclopentanone (Method B)

In a 3-L three necked flask fitted with a mechanical stirrer, a reflux condenser, a dropping funnel and a thermometer, are placed 83 g of 2-n-hexyl-cyclopentenone, 1.75 L 95% ethyl alcohol and 30 g of glacial acetic acid. The mixture is warmed up with sirring to 35°C and a solution of 65 g of potassium cyanide in 190 ml of water is added over a period of 15 minutes. Stirring is continued for 3 hours, the temperature being maintained at 35°C. The methanol is then distilled off at a reduced pressure the organic layer is separated, and the water phase is extracted with ether. The combined organic layer and other extract are washed with sodium carbonate solution and water and dried over anhydrous sodium sulphate. The solvent is removed at atmospheric pressure and the residue is distilled through a short Vigreux column. 2-n-Hexyl-3-cyanocyclopentanone is collected at 106°–110°C/0,2 mm, yield 85 g (88%), $n_D^{20}$ 1.4658.

The homologous cyclic ketonitriles listed in Table II, were prepared following method B.

TABLE I

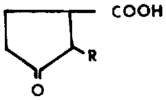

V

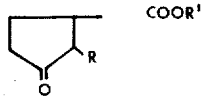

I

| Example | bromo-ester | R | R' | V m.p. | I b.p./mm Hg | $n_D^{20}$ |
|---|---|---|---|---|---|---|
| 5 | $C_4H_9CHBrCOOCH_3$ (1) | n-$C_4H_9$ | $CH_3$ | 45–46°C | 77°C/0.2 | 1.45 |
| 6 | $(CH_3)_2CHCH_2CHBrCOOC_2H_5$ (2) | iso-$C_4H_9$ | $CH_3$ | 85.5–86°C | 69°C/0.05 | 1.45 |
| 7 | 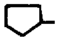 $CHBrCOOCH_3$ (3) | cyclo-$C_5H_9$ | $CH_3$ | — | 81°C/0.1 | 1.48 |
| 8 | $C_7H_{15}CHBrCOOC_2H_5$ (4) | n-$C_7H_{15}$ | $CH_3$ | 63–64°C | 90°C/0.1 | 1.45 |

(1) H. Reinheckel, Ber. 93, 2222 (1960)
(2) E. Testa et al. Helv. Chim. Acta 46, 766 (1963).
(3) Prepared from α-bromocyclpentylacetic acid (J. von Braun, Ber. 67B, 218 (1934), b.p. 67°C/1 mm, $n_D^{20}$ 1.4837
(4) B. Ackerman et al., J. Am. Chem. Soc. 79, 6524 (1957).

TABLE II

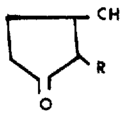

VII

| Example (1) | method | R | h.p./mm Hg | $n_D^{20}$ | yield |
|---|---|---|---|---|---|
| 11 | B | n-$C_4H_9$ | 96°C/0.7 | 1.4651 | 82% |
| 12 | B | n-$C_5H_{11}$ | 96–8°C/0.1 | 1.4657 | 87% |
| 13 | B | iso-$C_5H_{11}$ | 97°C/0.15 | 1.4648 | 89% |
| 14 | B | n-$C_7H_{15}$ | 114°C/0.2 | 1.4659 | 75% |

(1) The following 2-alkyl-2-cyclopentenones used for the preparation of compounds VII were prepared from the corresponding alkylidenecyclopentanones (G. Bardelli et al., Rec. Trav. Chim., 86, 481 (1967) according to the method of J. M. Conia, Bull. Soc. Chim. France, 8, 3327 (1968)).

| | |
|---|---|
| 2-n-butyl-2-cyclopentenone | (h.p. 42°C/0.02 mm; $n_D^{20}$ 1.4732) |
| 2-n-pentyl-2-cyclopentenone | (h.p. 64°C/0.04 mm; $n_D^{20}$ 1.4738) |
| 2-iso-pentyl-2-cyclopentenone | (h.p. 58°C/0.08 mm; $n_D^{20}$ 1.4724) |
| 2-n-hexyl-2-cyclopentenone | (h.p. 60°C/0.05 mm; $n_D^{20}$ 1.4724) |
| 2-n-heptyl-2-cyclopentenone | (h.p. 75°C/0.06 mm; $n_D^{20}$ 1.4722). |

EXAMPLE 15

Preparation of methyl 2-n-hexyl-3-oxo-cyclopentanecarboxylate

In a 100 ml round bottomed flask fitted with a mechanical stirrer and a reflux condenser, are placed 19.3 g 2-n-hexyl-3-cyanocyclopentanone, 3.2 g of methanol and 19 g of 2-n-hexyl-3-cyanocyclopentanone, 3.2 g of methanol and 19 g of p-toluene-sulfonic acid monohydrate. The reaction mixture is stirred at reflux temperature for 6 hours. The reaction mixture is then cooled to room temperature and poured into 200 ml of ice cold water. The organic layer is separated and the water phase is extracted with pentane. The combined organic layer and pentane extract are washed with sodium carbonate solution and water and dried over anhydrous sodium sulphate. The solvent is distilled off at atmospheric pressure and the residue is distilled through a short Vigreux column.

Methyl 2-n-hexyl-3-oxocyclopentanonecarboxylate is collected at 110°–112°C/0.6 mm, yield 16.4 (75%); Infrared spectrum coincides with that of the product obtained by the method described in Example 1(a).

EXAMPLE 16

Preparation of methyl 2-iso-pentyl-3-oxocyclopentanecarboxylate

In a 0.5-L three necked flask fitted with a reflux condenser, a mechanical stirrer, and a gas inlet tube, is placed a solution of 17.9 g of 2-iso-pentyl-3-cyanocyclopentanone and 2 ml of water in 200 ml of absolute methanol. Dry hydrogen chloride is passed through the refluxing solution for a period of 2 hours. The reaction mixture is maintained at reflux temperature for an additional hour. The methanol is distilled off at a reduced pressure and the residue is diluted with 300 ml of cold water. The organic layer is separated and the water phase is extracted with pentane. The combined organic layer and pentane extract are washed with sodium carbonate solution and water and dried over anhydrous sodium sulphate. The solvent is distilled off at atmospheric pressure and the residue is distilled through a short Vigreux column. Methyl 2-iso-pentyl-3-oxo-cyclopentanecarboxylate is collected at 94.5°C/0.7 mm, yield 14 g (67%), $n_D^{20}$ 1.4561.

EXAMPLE 17

Preparation of ethyl 2-iso-pentyl-3-oxo-cyclopentanecarboxylate

By repeating the procedure described in Example 16 but starting from 10 g 2-iso-pentyl-3-cyanocyclopentanone and 1 ml of water in 100 ml of absolute ethanol, there is obtained 7.3 g (58%) of ethyl 2-isopentyl-3-oxocyclopentanecarboxylate boiling at 84°C/0.25 mm, $n_D^{20}$ 1.4530.

EXAMPLE 18

Preparation of methyl 2-n-hexyl-3-oxocyclopentanecarboxylate

By repeating the procedure described in Example 16 but starting from 19.3 g of 2-n-hexyl-3-cyanocyclopentanone, there is obtained 16 g (72%) of methyl 2-n-hexyl-3-oxo-cyclopentanecarboxylate boiling at 100°C/0.15 mm, $n_D^{20}$ 1.4567.

EXAMPLE 19

Preparation of 2-n-hexyl-3-nitromethylcyclopentanone

In a 2-L flask fitted with a reflux condenser, is placed 332 g of 2-n-hexyl-2-cyclopentenone, 183 g of nitromethane, 30 ml of 40% methanolic solution of benzyltrimethylammonium hydroxide (Triton B) and 200 ml of dry dioxane. The reaction mixture is refluxed for 23 hours. The solvent is distilled off under a reduced pressure and the residue is dissolved in 1 L of ether. The ether solution is washed successively with dilute hydrochloric acid, water and sodium bicarbonate solution and dried over anhydrous sodium sulphate. The solvent is removed at atmospheric pressure and the residue is distilled through a short Vigreux column. After a lower boiling fraction (35 g, 65°C/0.2 mm) consisting of 2-n-hexyl-2-cyclopentenone, the product is collected at 135°C/0.3 mm, yield 365 g (80%), $n_D^{20}$ 1.4733.

The homologous cyclic nitroketones listed in Table III were prepared following the method described in Example 19.

TABLE III

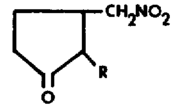

| Example | R | b.p./mmHg | $n_D^{20}$ | yield |
|---|---|---|---|---|
| 20 | n-$C_4H_9$ | 111–112°C/0.1 | 1.4745 | 79% |
| 21 | n-$C_5H_{11}$ | 121–123°C/0.25 | 1.4743 | 75% |
| 22 | n-$C_7H_{15}$ | 133–134°C/0.15 | 1.4727 | 77% |

EXAMPLE 23

Preparation of methyl 2-n-hexyl-3-oxo-cyclopentanecarboxylate

In a 0.5 L stainless steel autoclave, is placed a solution of 11.4 g of 2-n-hexyl-3-nitromethylcyclopentanone and 4.8 g of methanesulfonic acid in 100 ml of 80% methanol. The reaction mixture is maintained at 100°C for 24 hours. The solvent is distilled off at a reduced pressure and the residue is dissolved in ether. The ether solution is washed with sodium hydrogencarbonate solution and water and dried over anhydrous sodium sulphate. The ether is distilled off at atmospheric pressure and the residue is distilled through an efficient column. Methyl 2-n-hexyl-3-oxo-cyclopentanecarboxylate is collected at 102°C/0.2 mm, yield 6.2 g (55%); infrared spectrum coincides with that of the product obtained by the method described in Example 1(a).

EXAMPLE 24

Preparation of methyl 2-n-hexyl-3-oxo-cyclopentanecarboxylate

In a 0.5 L three necked flask fitted with a reflux condenser and a gas inlet tube, is placed a solution of 22.4 g of 2-n-hexyl-3-nitromethylcyclopentanone and 1.8 g of water in 180 ml of absolute methanol. Dry hydrogen chloride is passed through the refluxing solution for a period of 8 hours. The reaction mixture is maintained at reflux temperature for an additional hour. The methanol is distilled off at a reduced pressure and the residue is poured into 300 ml of cold water. The organic layer is separated and the water phase is extracted with ether. The combined organic layer and other extract are washed with sodium carbonate solution and water and dried over anhydrous sodium sulphate. The solvent is distilled off at atmospheric pressure. The crude reaction product which contains some methyl 2-n-hexyl-3-oxo-1-cyclopentanecarboxylate is purified by hydrogenation over 0.1 g of 10% Pd/C at 50 psi, to yield 11 g (49%) of methyl 2-n-hexyl-3-oxo-cyclopentanecarboxylate boiling at 100°C/0.15 mm.

We claim:

1. New compounds having the structure:

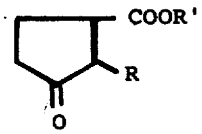

wherein R is selected from the group consisting of branched and straight-chained alkyl radicals containing from 4 to 8 carbon atoms and the cycloalkyl radicals cyclopentyl and cyclohexyl, and R′ represents an alkyl radical containing from 1 to 2 carbon atoms.

2. The compound of claim 1 which is methyl 2-n-butyl-3-oxo-cyclopentanecarboxylate.

3. The compound of claim 1 which is ethyl 2-n-butyl-3-oxo-cyclopentanecarboxylate.

4. The compound of claim 1 which is methyl 2-n-pentyl-3-oxo-cyclopentanecarboxylate.

5. The compound of claim 1 which is ethyl 2-n-pentyl-3-oxo-cyclopentanecarboxylate.

6. The compound of claim 1 which is methyl 2-(3′-methyl-butyl)-3-oxo-cyclopentanecarboxylate.

7. The compound of claim 1 which is ethyl 2-(3′-methyl-butyl)-3-oxo-cyclopentanecarboxylate.

8. The compound of claim 1 which is methyl 2-cyclopentyl-3-oxo-cyclopentanecarboxylate.

9. The compound of claim 1 which is methyl 2-n-hexyl-3-oxo-cyclopentanecarboxylate.

10. The compound of claim 1 which is ethyl 2-n-hexyl-3-oxo-cyclopentanecarboxylate.

11. The compound of claim 1 which is methyl 2-n-heptyl-3-oxo-cyclopentanecarboxylate.

* * * * *